(12) United States Patent
Cheng et al.

(10) Patent No.: US 6,936,744 B1
(45) Date of Patent: Aug. 30, 2005

(54) ALKYLAROMATICS PRODUCTION

(75) Inventors: Jane Chi Ya Cheng, Bridgewater, NJ (US); Michael Alan Steckel, Bethlehem, PA (US); Charles Morris Smith, West University Place, TX (US); William Alois Weber, Burlington, NJ (US); Stephen Harold Brown, Pennington, NJ (US); Ajit Bhaskar Dandekar, Marlton, NJ (US); Michael Alan Better, Kingwood, TX (US)

(73) Assignee: ExxonMobil Chemical Patents, Inc., Houston, TX (US)

( * ) Notice: Subject to any disclaimer, the term of this patent is extended or adjusted under 35 U.S.C. 154(b) by 0 days.

(21) Appl. No.: 09/619,560

(22) Filed: Jul. 19, 2000

(51) Int. Cl.⁷ ............................................ C07C 6/00
(52) U.S. Cl. ............................... 585/475; 585/470
(58) Field of Search ............................... 585/470, 475

(56) References Cited

U.S. PATENT DOCUMENTS

| | | | |
|---|---|---|---|
| 3,308,069 A | 3/1967 | Wadlinger et al. | 252/455 |
| 3,385,906 A * | 5/1968 | Kaufman | 260/671 |
| 3,449,070 A | 6/1969 | McDaniel et al. | 23/111 |
| 3,751,504 A | 8/1973 | Keown et al. | 260/672 |
| 3,766,093 A | 10/1973 | Chu | 252/455 |
| 3,894,104 A | 7/1975 | Chang et al. | 260/668 |
| 4,016,218 A | 4/1977 | Haag et al. | 260/671 |
| 4,415,438 A | 11/1983 | Dean et al. | 208/120 |
| 4,439,409 A | 3/1984 | Puppe et al. | 423/328 |
| 4,459,426 A * | 7/1984 | Inwood et al. | 585/323 |
| 4,547,605 A | 10/1985 | Kresge et al. | 585/467 |
| 4,774,377 A * | 9/1988 | Barger et al. | 585/323 |
| 4,826,667 A | 5/1989 | Zones et al. | 423/277 |
| 4,891,458 A | 1/1990 | Innes et al. | 585/323 |
| 4,954,325 A | 9/1990 | Rubin et al. | 423/328 |
| 4,992,606 A | 2/1991 | Kushnerick et al. | 585/467 |
| 5,236,575 A | 8/1993 | Bennett et al. | 208/46 |
| 5,250,277 A | 10/1993 | Kresge et al. | 423/329.1 |
| 5,334,795 A | 8/1994 | Chu et al. | 585/467 |
| 5,362,697 A | 11/1994 | Fung et al. | 502/71 |
| 5,557,024 A | 9/1996 | Cheng et al. | 585/467 |
| 5,789,641 A | 8/1998 | Alario et al. | 585/475 |

FOREIGN PATENT DOCUMENTS

| | | |
|---|---|---|
| EP | 0789009 | 8/1997 |
| WO | WO 200066520 | 11/2000 |

* cited by examiner

*Primary Examiner*—Walter D. Griffin
(74) *Attorney, Agent, or Firm*—D. M. Tyus; L. A. Kubena

(57) ABSTRACT

The present invention provides a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of said molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstrom.

24 Claims, No Drawings

ALKYLAROMATICS PRODUCTION

BACKGROUND OF THE INVENTION

The present invention relates to a process for producing alkylaromatics, particularly ethylbenzene and cumene.

Ethylbenzene and cumene are valuable commodity chemicals which are used industrially for the production of styrene monomer and coproduction of phenyl and acetone respectively. Ethylbenzene may be produced by a number of different chemical processes but one process which has achieved a significant degree of commercial success is the vapor phase alkylation of benzene with ethylene in the presence of a solid, acidic ZSM-5 zeolite catalyst. Examples of such ethylbenzene production processes are described in U.S. Pat. Nos. 3,751,504 (Keown), 4,547,605 (Kresge), and 4,016,218 (Haag).

More recently focus has been directed at liquid phase processes for producing ethylbenzene from benzene and ethylene since liquid phase processes operate at a lower temperature than their vapor phase counterparts and hence tend to result in lower yields of by-products. For example, U.S. Pat. No. 4,891,458 describes the liquid phase synthesis of ethylbenzene with zeolite beta, whereas U.S. Pat. No. 5,334,795 describes the use of MCM-22 in the liquid phase synthesis of ethylbenzene.

Cumene has for many years been produced commercially by the liquid phase alkylation of benzene with propylene over a Friedel-Craft catalyst, particularly solid phosphoric acid or aluminum chloride. More recently, however, zeolite-based catalyst systems have been found to be more active and selective for propylation of benzene to cumene. For example, U.S. Pat. No. 4,992,606 describes the use of MCM-22 in the liquid phase alkylation of benzene with propylene.

Existing alkylation processes for producing ethylbenzene and cumene inherently produce polyalkylated species as well as the desired monoalkyated product. It is therefore normal to transalkylate the polyalkylated species with benzene to produce additional ethylbenzene or cumene either by recycling the polyalkylated species to the alkylation reactor or, more frequently, by feeding the polyalkylated species to a separate transalkylation reactor. Examples of catalysts which have been proposed for use in the transalkylation of polyalkylated species, such as polyethylbenzenes and polyisopropylbenzenes, are listed in U.S. Pat. No. 5,557,024 and include MCM-49, MCM-22, PSH-3, SSZ-25, zeolite X, zeolite Y, zeolite beta, acid dealuminized mordenite and TEA-mordenite. Transalkylation over a small crystal (<0.5 micron) form of TEA-mordenite is also disclosed in U.S. patent application Ser. No. 09/305,019 filed May 4, 1999.

Where the alkylation step is performed in the liquid phase, it is also desirable to conduct the transalkylation step under liquid phase conditions. However, by operating at relatively low temperatures, liquid phase processes impose increased requirements on the catalyst, particularly in the transalkylation step where the bulky polyalkylated species must be converted to additional monoalkylated product without producing unwanted by-products. This has proved a significant problem in the case of cumene production where existing catalysts have either lacked the desired activity or have resulted in the production of significant quantities of by-products such as ethylbenzene and n-propylbenzene.

According to the invention, it has now unexpectedly been found that a specific mixed catalyst system has a unique combination of activity and selectivity when used as a liquid phase transalkylation catalyst, particularly for the liquid phase transalkylation of polyisopropylbenzenes to cumene.

SUMMARY OF THE INVENTION

According to one aspect of the invention, there is provided a process for producing a monoalkylated aromatic compound comprising the step of contacting a polyalkylated aromatic compound with an alkylatable aromatic compound under at least partial liquid phase conditions and in the presence of a transalkylation catalyst to produce a monoalkylated aromatic compound, wherein the transalkylation catalyst comprises a mixture of at least two different crystalline molecular sieves, wherein each of said molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstrom.

Preferably, said transalkylation catalyst comprises a mixture of at least:

(i) a first crystalline molecular sieve having a X-ray diffraction pattern including d-spacing maxima at 12.4±0.25, 6.9±0.15, 3.57±0.07 and 3.42±0.07 Angstrom; and (ii) a second crystalline molecular sieve different from the first molecular sieve and selected from zeolite beta, zeolite Y and mordenite.

Preferably, the first crystalline molecular sieve is selected from MCM-22, MCM-36, MCM-49, and MCM-56.

Preferably, the second crystalline molecular sieve is TEA-mordenite having an average crystal size of less than 0.5 micron.

Preferably, the alkyl groups of the polyalkylated aromatic compound have 1 to 5 carbon atoms.

In a further aspect, the invention resides in a process for producing a monoalkylated aromatic compound comprising the steps of:

(a) contacting an alkylatable aromatic compound with an alkylating agent in the presence of an alkylation catalyst to provide a product comprising said monoalkylated aromatic compound and a polyalkylated aromatic compound, and then (b) contacting the polyalkylated aromatic compound from step (a) with said alkylatable aromatic compound under at least partial liquid phase conditions and in the presence of a transalkylation catalyst to produce a monoalkylated aromatic compound, wherein the transalkylation catalyst comprises a mixture of at least two different crystalline molecular sieves, wherein each of said molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstrom.

Preferably, the alkylation step (a) is conducted under at least partial liquid phase conditions.

Preferably, the alkylating agent includes an alkylating aliphatic group having 1 to 5 carbon atoms.

Preferably, the alkylating agent is ethylene or propylene and the alkylatable aromatic compound is benzene.

Preferably, the alkylation catalyst of step (a) is selected from MCM-22, MCM-49, MCM-56 and zeolite beta.

DETAILED DESCRIPTION OF THE INVENTION

The present invention relates to a process for the production of a monoalkylated aromatic compound, particularly ethylbenzene and cumene, by the liquid phase transalkylation of the polyalkylated derivative with an alkylatable compound, particularly benzene, over a particular mixed transalkylation catalyst. More particularly, the invention is concerned with a process in which the liquid phase transalkylation step follows an alkylation step, which may also be carried out in the liquid phase and in which the alkylatable compound is reacted with an alkylating agent, particularly ethylene and propylene, to produce the required monoalkylated aromatic end product as well as the polyalkylated derivative, which is separated and fed to the transalkylation step.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a heteroatom are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene, with benzene being preferred.

Generally the alkyl groups which can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes make in such instances may be less than about 500 ppm.

Reformate containing substantial quantities of benzene, toluene and/or xylene constitutes a particularly useful feed for the alkylation process of this invention.

The alkylating agents which are useful in the process of this invention generally include any aliphatic or aromatic organic compound having one or more available alkylating aliphatic groups capable of reaction with the alkylatable aromatic compound, preferably with the alkylating group possessing from 1 to 5 carbon atoms. Examples of suitable alkylating agents are olefins such as ethylene, propylene, the butenes, and the pentenes; alcohols (inclusive of monoalcohols, dialcohols, trialcohols, etc.) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides, and the pentyl chlorides, and so forth.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins, refinery FCC propane/propylene streams, etc., are useful alkylating agents herein. For example, a typical FCC light olefin stream possesses the following composition:

|  | Wt. % | Mole % |
|---|---|---|
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Reaction products which may be obtained from the process of the invention include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes. Preferably, the process of the invention relates to the production of cumene by the alkylation of benzene with propylene followed by the transalkylation of the polyisopropylbenzene by-products with additional benzene.

The alkylation process of this invention is conducted such that the organic reactants, i.e., the alkylatable aromatic compound and the alkylating agent, are brought into contact with an alkylation catalyst in a suitable reaction zone such as, for example, in a flow reactor containing a fixed bed of the catalyst composition, under effective alkylation conditions. Such conditions include a temperature of from about 0° C. to about 500° C., and preferably between about 50° C. and about 250° C., a pressure of from about 0.2 to about 250 atmospheres, and preferably from about 5 to about 100 atmospheres, a molar ratio of alkylatable aromatic compound to alkylating agent of from about 0.1:1 to about 50:1, and preferably can be from about 0.5:1 to about 10:1, and a feed weight hourly space velocity (WHSV) of between about 0.1 and 500 $hr^{-1}$, preferably between 0.5 and 100 $hr^{-1}$.

The reactants can be in either the vapor phase or partially or completely in the liquid phase and can be neat, i.e., free from intentional admixture or dilution with other material, or they can be brought into contact with the zeolite catalyst composition with the aid of carrier gases or diluents such as, for example, hydrogen or nitrogen.

When benzene is alkylated with ethylene to produce ethylbenzene, the alkylation reaction is preferably carried out in the liquid phase under conditions including a temperature between 300° and 600° F. (about 150° and 316° C.), more preferably between 400° F. and 500° F. (about 205° C. and 260° C.), a pressure up to about 3000 psig (20875 kPa), more preferably between 400 and 800 psig (2860 and 5600 kPa), a space velocity between about 0.1 and 20 WHSV, more preferably between 1 and 6 WHSV, based on the ethylene feed, and a ratio of the benzene to the ethylene in the alkylation reactor from 1:1 to 30:1 molar, more preferably from about 1:1 to 10:1 molar.

When benzene is alkylated with propylene to produce cumene, the reaction may also take place under liquid phase conditions including a temperature of up to about 250° C., e.g., up to about 150° C., e.g., from about 10° C. to about 125° C.; a pressure of about 250 atmospheres or less, e.g., from about 1 to about 30 atmospheres; and an aromatic hydrocarbon weight hourly space velocity (WHSV) of from about 5 $hr^{-1}$ to about 250 $hr^{-1}$, preferably from 5 $hr^{-1}$ to 50 $hr^{-1}$.

The alkylation catalyst is a crystalline molecular sieve preferably selected from MCM-22 (described in detail in U.S. Pat. No. 4,954,325), MCM-49 (described in detail in U.S. Pat. No. 5,236,575), MCM-56 (described in detail in U.S. Pat. No. 5,362,697), and zeolite beta (described in detail in U.S. Pat. No. 3,308,069). The molecular sieve can be combined in conventional manner with an oxide binder, such as alumina, such that the final alkylation catalyst contains between 2 and 80 wt % sieve.

The alkylation reactor effluent contains the excess aromatic feed, monoalkylated product, polyalkylated products, and various impurities. The aromatic feed is recovered by distillation and recycled to the alkylation reactor. Usually a small bleed is taken from the recycle stream to eliminate unreactive impurities from the loop. The bottoms from the benzene distillation are further distilled to separate monoalkylated product from polyalkylated products and other heavies.

The polyalkylated products separated from the alkylation reactor effluent are reacted with additional aromatic feed in a transalkylation reactor, separate from the alkylation reactor, over a suitable transalkylation catalyst. According to the invention, the transalkylation catalyst is a mixture of at least two different crystalline molecular sieves, wherein each of said molecular sieves is selected from zeolite beta, zeolite Y, mordenite and a further material having an X-ray diffraction pattern including d-spacing maxima at 12.4±0.25, 6.9±0.15, 3.57±0.07 and 3.42±0.07 Angstrom.

The X-ray diffraction data used to characterize said further material of the mixed transalkylation catalyst of the invention are obtained by standard techniques using the K-alpha doublet of copper as the incident radiation and a diffractometer equipped with a scintillation counter and associated computer as the collection system. Materials having the required X-ray diffraction lines include MCM-22 (described in U.S. Pat. No. 4,954,325), PSH-3 (described in U.S. Pat. No. 4,439,409), SSZ-25 (described in U.S. Pat. No. 4,826,667), MCM-36 (described in U.S. Pat. No. 5,250,277), MCM-49 (described in U.S. Pat. No. 5,236,575) and MCM-56 (described in U.S. Pat. No. 5,362,697), with MCM-22 being particularly preferred.

Preferably, the transalkylation catalyst comprises a mixture of at least:
(iii) a first crystalline molecular sieve having a X-ray diffraction pattern including d-spacing maxima at 12.4±0.25, 6.9±0.15, 3.57±0.07 and 3.42±0.07 Angstrom; and
(iv) a second crystalline molecular sieve different from the first molecular sieve and selected from zeolite beta, zeolite Y and mordenite.

Zeolite beta is disclosed in U.S. Pat. No. 3,308,069. Zeolite Y and mordenite occur naturally but may also be used in one of their synthetic forms, such as Ultrastable Y (USY), which is disclosed in U.S. Pat. No. 3,449,070, Rare earth exchanged Y (REY), which is disclosed in U.S. Pat. No. 4,415,438, and TEA-mordenite (i.e., synthetic mordenite prepared from a reaction mixture comprising a tetraethylammonium directing agent), which is disclosed in U.S. Pat. Nos. 3,766,093 and 3,894,104. However, in the case of TEA-mordenite, the particular synthesis regimes described in the patents noted lead to the production of a mordenite product composed of predominantly large crystals with a size greater than 1 micron and typically around 5 to 10 micron. It has been found that controlling the synthesis so that the resultant TEA-mordenite has an average crystal size of less than 0.5 micron results in a catalyst with materially enhanced activity for liquid phase aromatics transalkylation.

The required small crystal TEA-mordenite can be produced by crystallization from a synthesis mixture having a molar composition within the following ranges:

|  | Useful | Preferred |
| --- | --- | --- |
| R/R + $Na^+$ = | >0.4 | 0.45–0.7 |
| $OH^-/SiO_2$ = | <0.22 | 0.05–0.2 |
| $Si/Al_2$ = | >30–90 | 35–50 |
| $H_2O/OH$ = | 50–70 | 50–60 |

The crystallization is conducted at a temperature of 90 to 200° C., for a time of 6 to 180 hours.

The mixed transalkylation catalyst of the invention preferably comprises about 10 to about 75% by weight, and more preferably about 15 to about 50% by weight, of first crystalline molecular sieve and about 10 to about 75% by weight, and more preferably about 15 to about 50% by weight, of the second crystalline molecular sieve, based on the total weight of molecular sieve material in the catalyst.

The mixed transalkylation catalyst of the invention may also include a matrix or binder which is composited with the inorganic oxide material. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the inorganic oxide material include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the inorganic oxide material employed herein may be composited with a porous matrix material, such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

The relative proportions of inorganic oxide material and binder may vary widely with the inorganic oxide material content ranging from about 1 to about 90 percent by weight and more usually in the range of about 30 to about 80 percent by weight of the total catalyst.

The mixed transalkylation catalyst of the invention may be produced by physically mixing the different molecular sieve components prior to catalyst particle formation, by mixing separate catalyst particles containing the different molecular sieve components or may be produced by coextruding the different molecular sieve components, normally with a binder.

The transalkylation reaction of the invention is conducted under at least partial liquid phase conditions such that the polyalkylated aromatics react with the additional aromatic feed to produce additional monoalkylated product. Suitable transalkylation conditions include a temperature of 100 to 260° C., a pressure of 10 to 50 barg (1100–5100 kPa), a weight hourly space velocity of 1 to 10 on total feed, and benzene/polyalkylated benzene weight ratio 1:1 to 6:1.

When the polyalkylated aromatics are polyethylbenzenes and are reacted with benzene to produce ethylbenzene, the transalkylation conditions preferably include a temperature of 220 to 260° C., a pressure of 20 to 30 barg, weight hourly space velocity of 2 to 6 on total feed and benzene/PEB weight ratio 2:1 to 6:1.

When the polyalkylated aromatics are polyisopropylbenzenes and are reacted with benzene to produce cumene, the transalkylation conditions preferably include a temperature of 100 to 200° C., a pressure of 20 to 30 barg, weight hourly space velocity of 1 to 10 on total feed and benzene/PEB weight ratio 1:1 to 6:1.

The effluent from the transalkylation reactor is blended with alkylation reactor effluent and the combined stream distilled to separate the desired monoalkylated product.

The invention will be described with reference to the following Examples.

EXAMPLE 1

Feed Preparation

Benzene (chemical grade) and polyisopropylbenzene (obtained from a commercial cumene unit) were purified by percolation over activated alumina. The purified benzene and polyisopropylbenzene were mixed in 2:1 weight ratio and stored under nitrogen. A GC analysis of the feed showed the following composition by weight.

| | |
|---|---|
| Lights | 0.011 |
| Benzene | 65.628 |
| Toluene | 0.010 |
| Cumene | 0.078 |
| m-Diisopropybenzene | 8.520 |
| o- Diisopropybenzene | 1.327 |
| p- Diisopropybenzene | 3.298 |
| Other C12 aromatics | 0.789 |
| C15 aromatics | 0.338 |
| Sum, wt % | 100.000 |

EXAMPLE 2

Cumene Synthesis Via Benzene/Polyisopropylbenzene Transalkylation Over Zeolite Beta 2.0 g of zeolite beta (1/16" [1.6 mm] diameter extrudates with 35% $Al_2O_3$ binder chopped to 1/16" [1.6 mm] length) was used for transalkylation of the feed of Example 1. The catalyst was diluted with sand to 5.5 cc and charged to an isothermal, down-flow, 3/8" [9.5 mm] outside diameter fixed-bed reactor. The catalyst was dried at 125° C. and atmospheric pressure with 100 cc/min flowing $N_2$ for 2 hours. The $N_2$ was turned off and reactor pressure was set to 300 psig (2170 kPa) by a grove loader. The feed described in Example 1 was introduced into the reactor at 60 cc/hr for 1 hour and then at 2.0 total WHSV (based on total catalyst weight). During the initial high flow of the feed, the reactor temperature was ramped at 5° C./min to 180° C. After lining out, liquid products were collected in a cold-trap and analyzed off-line with an HP 5890 GC. Diisopropylbenzene (DIPB) conversion at 2.0 WHSV was 55%. The catalyst was further tested at 2.2 and 2.4 WHSV under otherwise identical conditions, and DIPB conversions of 53% and 50%, respectively, were obtained. Catalyst performance at 50% DIPB conversion is shown in Table 1.

EXAMPLE 3

Cumene Synthesis Via Benzene/Polyisopropylbenzene Transalkylation Over MCM-22

2.5 g of MCM-22 (1/16" [1.6 mm] diameter extrudates with 35% $Al_2O_3$ binder and chopped to 1/16" [1.6 mm] length) was used for transalkylation of the feed of Example 1. The catalyst was diluted with sand to 7 cc and charged to the reactor. The catalyst was tested at 2.0 and 1.1 WHSV in the same manner as described in Example 2, with the DIPB conversion being 30% and 50%, respectively. Catalyst performance at 50% DIPB conversion is shown in Table 1.

EXAMPLE 4

Cumene Synthesis Via Benzene/Polyisopropylbenzene Transalkylation Over TEA-Mordenite TEA-mordenite was prepared from a synthesis mixture which comprised water, aluminum sulfate solution, sodium hydroxide and tetraethylammonium bromide and which had the following molar composition (based alumina=1):

| | |
|---|---|
| silica = | 39.7 |
| $Na_2O$ = | 7.3 |
| $SO_4$ = | 2.9 |
| TEA = | 12.3 |
| water = | 370 |

The synthesis mixture was crystallized at 149° C. (300° F.) with stirring at 90 RPM for 40–44 hrs. The resultant TEA-mordenite was isolated by filtration, washed and dried and found to have a crystal size by scanning electron microscopy of <0.5 micron.

A catalyst was prepared by compositing the resultant TEA-mordenite with 35% $Al_2O_3$ binder and extruding the composite into a ¹⁄₁₆" [1.6 mm] diameter cylindrical extrudate. The extrudate was chopped to ¹⁄₁₆" [1.6 mm] length and 1.0 g of the resultant catalyst was used for transalkylation of the feed of Example 1. The catalyst was diluted with sand to 3 cc and charged to the reactor. The same procedure described in Example 2 was followed to start the run. The catalyst was tested at 4.0, 5.3, and 6.3 total WHSV, and DIPB conversions of 66%, 60%, and 52%, respectively, were obtained. Catalyst performance at 52% DIPB conversion is shown in Table 1.

EXAMPLE 5

Cumene Synthesis Via
Benzene/Polyisopropylbenzene Transalkylation
Over a 1:1 MCM-22 and TEA-Mordenite Catalyst
Mixture 1.0 g of MCM-22 and 1.0 g of TEA-mordenite, as described in examples 3 and 4, were mixed thoroughly and used for transalkylation. The catalyst mixture was diluted with sand to 5.5 cc and charged to the reactor. The same procedure described in Example 2 was followed to start the run. The catalyst was tested at 3.0 total WHSV (based on 2 g of catalysts) and DIPB conversion was 51%. Catalyst performance at this conversion level is shown in Table 1.

EXAMPLE 6

Cumene Synthesis Via
Benzene/Polyisopropylbenzene Transalkylation
Over a 1:1 MCM-22 and TEA-Mordenite
Coextruded Catalyst An alumina-bound co-extruded MCM-22 and TEA-Mordenite catalyst was prepared as described below. As-synthesized MCM-22 with a silica-to-alumina ratio of 25 and as-synthesized TEA-Mordenite with a silica-to-alumina ratio of 37 were used for catalyst preparation. A physical mixture of 40 parts MCM-22, 40 parts TEA-Mordenite and 20 parts pseudoboehmite alumina was mulled to form a uniform mixture. All components were blended based on parts by weight on a 100% solids basis. Sufficient amount of deionized water was added to form an extrudable paste. The mixture was auger extruded to ¹⁄₂₀" quadrulobe shape extrudates and dried at 121° C. overnight. The dried extrudates were calcined in inert atmosphere and exchanged with $NH_4NO_3$ solution, followed by final air calcination to make the H-form. The H-form final catalyst had a hexane cracking activity of 350 alpha. 2.0 g of the coextruded catalyst prepared above was mixed thoroughly and used for transalkylation. The catalyst was diluted with sand to 5.5 cc and charged to the reactor. The same procedure described in Example 2 was followed to start the run. The catalyst was tested at 3.0 total WHSV and DIPB conversion was 53%. Catalyst performance at this conversion level is shown in Table 1.

EXAMPLE 7

Cumene Synthesis Via
Benzene/Polyisopropylbenzene Transalkylation
Over a 1:1 MCM-22 and Beta Catalyst Mixture 1.0 g of MCM-22 and 1.0 g of beta, as described in examples 2 and 3, were mixed thoroughly and used for transalkylation. The catalyst mixture was diluted with sand to 5.5 cc and charged to the reactor. The same procedure described in Example 2 was followed to start the run. The catalyst was tested at 1.5 and 1.3 WHSV (based on 2 g of catalysts) in the same manner as described in Example 2, and the DIPB conversions were 36% and 52%, respectively. Catalyst performance at 52% DIPB conversion is shown in Table 1.

TABLE 1

| Catalyst | Example 2 Beta | Example 3 MCM-22 | Example 4 TEA-Mordenite | Example 5 1:1 MCM-22 and TEA-Mordenite Physical Mixture | Example 6 1:1 MCM-22 and TEA-Mordenite Coextruded | Example 7 1:1 MCM-22 and Beta Physical Mixture |
|---|---|---|---|---|---|---|
| WHSV | 2.4 | 1.1 | 6.3 | 3.0 | 3.0 | 1.3 |
| Days on Stream | 9.9 | 8.9 | 5.9 | 4.9 | 10.9 | 5.9 |
| DIPB Conv, % | 49.5 | 50.3 | 52.2 | 51.3 | 53.2 | 52.4 |
| TIPB Conv, % | 10.6 | 26.8 | −1.4 | 9.5 | 27.9 | 27.8 |
| m-DIPB Conv, % | 41.1 | 37.6 | 47.8 | 43.3 | 45.7 | 44.2 |
| o-DIPB Conv, % | 69.9 | 93.4 | 2.5 | 75.6 | 64.2 | 93.5 |
| p-DIPB Conv, % | 59.1 | 63.7 | 63.3 | 60.2 | 62.8 | 62.2 |
| Cumene Sel, % | 98.2 | 98.5 | 99.2 | 99.0 | 99.3 | 98.6 |
| n-C3-Bz/Cum, ppm | 766 | 1056 | 870 | 777 | 722 | 644 |
| EB/Cum, ppm | 96 | 384 | 124 | 173 | 120 | 176 |
| Selectivity, wt % | | | | | | |
| Lights | 0.708 | 0.859 | 0.286 | 0.325 | 0.199 | 0.606 |
| Toluene | 0.004 | 0.009 | 0.008 | 0.012 | 0.004 | 0.006 |
| EB | 0.009 | 0.038 | 0.012 | 0.017 | 0.012 | 0.017 |
| Cumene | 98.184 | 98.451 | 99.233 | 99.043 | 99.339 | 98.603 |
| n-C3-Bz | 0.075 | 0.104 | 0.086 | 0.077 | 0.072 | 0.064 |
| 2,2-DiPh-C3 | 0.648 | 0.203 | 0.238 | 0.218 | 0.136 | 0.370 |
| Cumene dimer | 0.277 | 0.279 | 0.078 | 0.210 | 0.159 | 0.323 |
| Others | 0.094 | 0.057 | 0.057 | 0.098 | 0.080 | 0.011 |
| Sum | 100.00 | 100.00 | 100.00 | 100.00 | 100.00 | 100.00 |

The results in Table 1 show that, to achieve a constant DIPB conversion of about 50%, beta can be operated at 2.4 WHSV, MCM-22 at 1.1, and TEA-mordenite at 6.3 WHSV. Mixing TEA-mordenite and MCM-22 in 1:1 weight ratio, either as a physical mixture or as a coextruded catalyst, provided an active catalyst which could be operated at 3.0 WHSV to give the same DIPB conversion.

When used alone, MCM-22 was very active to convert o-DIPB and TIPB, but the EB and n-propylbenzene impurities were high. On the contrary, TEA-mordenite was inactive to convert o-DIPB and TIPB, but the EB and n-propylbenzene impurities were low. When used as a mixture, either as a physical mixture or as a coextruded catalyst, the MCM-22/TEA-mordenite system effectively converted o-DIPB and TIPB with 99+% cumene selectivity, with the coextruded catalyst exhibiting both increased activity and cumene selectivity as compared with the physical mixture. The overall impurities, including EB and n-propylbenzene, were low with the MCM-22/TEA-mordenite mixture.

When used alone, beta was a quite effective catalyst, but its 2,2-diphenylpropane impurity was high. When used as an MCM-22/beta mixture, the combined catalyst system effectively converted o-DIPB and TIPB with a conversion level matching that of MCM-22. The mixed catalyst also effectively reduced EB and n-propylbenzene impurities when compared to MCM-22 used alone. In addition, the mixed catalyst significantly reduced the 2,2-diphenylpropane impurity when compared to beta used alone.

What is claimed is:

1. A process for producing a monoalkylated aromatic compound comprising the step of contacting a polyalkylated aromatic compound with an alkylatable aromatic compound under at least partial liquid phase conditions and in the presence of a transalkylation catalyst to produce a monoalkylated aromatic compound, wherein the transalkylation catalyst comprises a mixture of at least:
   (i) a first crystalline molecular sieve having an X-ray diffraction pattern including d-spacing maxima at 12.4±0.25, 6.9+0.15, 3.57±0.07 and 3.42±0.07 Angstrom; and
   (ii) a second crystalline molecular sieve different from the first molecular sieve and selected from zeolite beta and mordenite.

2. The process of claim 1, wherein the first crystalline molecular sieve is selected from MCM-22, MCM-36, MCM-49 and MCM-56.

3. The process of claim 1, wherein the second crystalline molecular sieve comprises TEA-mordenite having an average crystal size of less than 0.5 micron.

4. The process of claim 1, wherein the transalkylation catalyst comprises about 15 to about 50% by weight of the first crystalline molecular sieve based on the total weight of molecular sieve material in the catalyst.

5. The process of claim 1, wherein the transalkylation catalyst is produced by coextrusion of said mixture of at least two different crystalline molecular sieves.

6. The process of claim 1, wherein the alkyl groups of the polyalkylated aromatic compound have 1 to 5 carbon atoms.

7. The process of claim 1, wherein the polyalkylated aromatic compound is polyisopropylbenzene and the alkylatable aromatic compound is benzene.

8. The process of claim 1, wherein said contacting step is conducted at a temperature of 100 to 260° C., a pressure of to 10 to 50 barg (1100 to 5100 kPa), and a weight hourly space velocity of 1 to 10 on total feed, and a weight ratio of alkylatable aromatic compound to polyalkylated aromatic compound of 1:1 to 6:1.

9. A process for producing a monoalkylated aromatic compound comprising the steps of:
   (a) contacting an alkylatable aromatic compound with an alkylating agent in the presence of an alkylation catalyst to provide a product comprising said monoalkylated aromatic compound and a polyalkylated aromatic compound, and then
   (b) contacting the polyalkylated aromatic compound from step (a) with said alkylatable aromatic compound under at least partial liquid phase conditions and in the presence of a transalkylation catalyst to produce a monoalkylated aromatic compound, wherein the transalkylation catalyst comprises a mixture of at least:
      (i) a first crystalline molecular sieve having an X-ray diffraction pattern including d-spacing maxima at 12.4±0.25, 6.9±0.15, 3.57±0.07 and 3.42±0.07 Angstrom; and
      (ii) a second crystalline molecular sieve different from the first molecular sieve and selected from zeolite beta and mordenite.

10. The process of claim 9, wherein the alkylation step (a) is conducted under at least partial liquid phase conditions.

11. The process of claim 9, wherein the alkylating agent includes an alkylating aliphatic group having 1 to 5 carbon atoms.

12. The process of claim 9, wherein the alkylating agent is propylene and the alkylatable aromatic compound is benzene.

13. The process of claim 9, wherein the alkylation catalyst of step (a) is selected from MCM-22, MCM-49, MCM-56 and zeolite beta.

14. The process of claim 9, wherein the first crystalline molecular sieve of the transalkylation catalyst of step (b) is selected from MCM-22, MCM-36, MCM-49 and MCM-56.

15. The process of claim 9, wherein the second crystalline molecular sieve of the transalkylation catalyst of step (b) comprises TEA-mordenite having an average crystal size of less than 0.5 micron.

16. The process of claim 9, wherein the transalkylation catalyst of step (b) comprises about 15 to about 50% by weight of the first crystalline molecular sieve based on the total weight of molecular sieve material in the catalyst.

17. A process for producing cumene comprising the steps of:
   (a) contacting benzene with propylene under at least partial liquid phase conditions and in the presence of an alkylation catalyst to provide a product comprising cumene and polyisopropylbenzenes, and then
   (b) contacting the polyisopropylbenzenes from step (a) with benzene under at least partial liquid phase conditions and in the presence of a transalkylation catalyst to produce further cumene, wherein the transalkylation catalyst comprises a mixture of at least:
      (i) a first crystalline molecular sieve having an X-ray diffraction pattern including d-spacing maxima at 12.4±0.25, 6.9±0.15, 3.57±0.07 and 3.42±0.07 Angstrom; and
      (ii) a second crystalline molecular sieve different from the first molecular sieve and selected from zeolite beta and mordenite.

18. The process of claim 1, wherein the first crystalline molecular sieve is MCM-22.

19. The process of claim 18 wherein the second crystalline molecular sieve is TEA-mordenite.

20. The process of claim 9, wherein the first crystalline molecular sieve is MCM-22 and the second crystalline molecular sieve is TEA-mordenite.

21. The process of claim 1, wherein the transalkylation catalyst comprises about 15 to about 50% by weight of the second crystalline molecular sieve based on the total weight of molecular sieve material in the catalyst.

22. The process of claim 9, wherein the transalkylation catalyst comprises about 15 to about 50% by weight of the second crystalline molecular sieve based on the total weight of molecular sieve material in the catalyst.

23. The process of claim 1, wherein the transalkylation catalyst comprises about 30 to about 50% by weight of the first crystalline molecular sieve based on the total weight of molecular sieve material in the catalyst.

24. The process of claim 9, wherein the transalkylation catalyst comprises about 30 to about 50% by weight of the first crystalline molecular sieve based on the total weight of molecular sieve material in the catalyst.

\* \* \* \* \*